United States Patent
Ito et al.

(10) Patent No.: US 7,883,719 B2
(45) Date of Patent: Feb. 8, 2011

(54) PASTING AGENT

(75) Inventors: Takeshi Ito, Tsukuba (JP); Tetsuro Tateishi, Tsukuba (JP); Naruhito Higo, Tsukuba (JP)

(73) Assignee: Hisamitsu Pharmaceutical Co., Inc., Tosu-shi, Saga (JP)

( * ) Notice: Subject to any disclaimer, the term of this patent is extended or adjusted under 35 U.S.C. 154(b) by 702 days.

(21) Appl. No.: 10/525,644

(22) PCT Filed: Aug. 7, 2003

(86) PCT No.: PCT/JP03/10090

§ 371 (c)(1),
(2), (4) Date: Mar. 17, 2005

(87) PCT Pub. No.: WO2004/019930

PCT Pub. Date: Mar. 11, 2004

(65) Prior Publication Data

US 2006/0165763 A1    Jul. 27, 2006

(30) Foreign Application Priority Data

Aug. 28, 2002  (JP)  ............................. 2002-249413

(51) Int. Cl.
*A61L 15/44* (2006.01)
*A61F 13/02* (2006.01)
*A61K 8/02* (2006.01)

(52) U.S. Cl. ...................... 424/448; 424/449

(58) Field of Classification Search .......... 424/443–449
See application file for complete search history.

(56) References Cited

U.S. PATENT DOCUMENTS 4,994,267 A * 2/1991 Sablotsky .................... 514/182
5,614,211 A * 3/1997 Gale et al. ................... 424/448
5,866,157 A * 2/1999 Higo et al. ................... 424/448
6,210,705 B1 * 4/2001 Mantelle et al. ............. 424/448
2002/0058068 A1 * 5/2002 Houze et al. ................. 424/487
2004/0028724 A1 * 2/2004 Terahara et al. ............. 424/449

FOREIGN PATENT DOCUMENTS

| EP | 0 760 238 A1 | 3/1997 |
| EP | 0 913 158 A1 | 5/1999 |
| EP | 1201232 A1 * | 5/2002 |
| JP | 04-266821 | 9/1992 |
| JP | 09-301854 | 11/1997 |
| JP | 09-315957 A | 12/1997 |
| JP | 11152224 | 6/1999 |
| JP | 2000007559 | 1/2000 |
| JP | 2001048783 | 2/2001 |
| JP | 4213432 B2 | 3/2004 |
| JP | 4261911 B2 | 5/2009 |
| WO | 95/31190 | 11/1995 |
| WO | WO 02/38139 | 5/2002 |
| WO | WO 02/38139 A1 * | 5/2002 |
| WO | 02/45666 A2 | 6/2002 |
| WO | WO 02/45699 | 6/2002 |
| WO | WO 02/069942 | 9/2002 |

OTHER PUBLICATIONS

The Office Action issued on Jun. 4, 2010 in a counterpart Korean patent Application, six (6) pages.

* cited by examiner

*Primary Examiner*—Carlos A Azpuru
*Assistant Examiner*—Melissa S Mercier
(74) *Attorney, Agent, or Firm*—The Nath Law Group; Susanne M. Hopkins; Ari G. Zytcer

(57) ABSTRACT

A patch comprising a backing layer and an adhesive layer disposed on the backing layer and compounded with an adhesive agent and oxybutynin and/or a pharmaceutically acceptable salt thereof, wherein the adhesive agent comprises an acrylic polymer substantially free of both carboxyl group and hydroxyl group and a rubber polymer, in which weight ratio of content of the acrylic polymer to content of the rubber polymer is from 1:4 to 1:19.

5 Claims, No Drawings

PASTING AGENT

This Application is the National Phase of International Application No. PCT/JP03/10090 filed Aug. 7, 2003, which designated the U.S. and was not published under PCT Article 21(2) in English, and this application claims, via the aforesaid International Application, the foreign priority benefit of and claims the priority from Japanese Application P2002-249413, filed Aug. 28, 2002, the complete disclosures of which are incorporated herein by reference.

TECHNICAL FIELD

The present invention relates to a patch, and more specifically to a patch employing oxybutynin.

BACKGROUND ART

Conventionally, concerning an administration method of medicine, the oral administration method using a tablet, a capsule, a syrup or the like has been known. However; in these years, an approach is tried in which these medicines are transdermally administrated by using a patch. The administration method using a patch can dissolve problems in the oral administration method and, in addition, has such advantages as decrease of administration frequency, enhancement of compliance, easiness of administration and discontinuation thereof. Therefore, it is expected as a useful administration method especially for the case where patients are aged persons or children.

However, the stratum corneum of the normal skin has a barrier function of inhibiting exogenous materials from penetrating into the body. Due to the barrier function, compounded medicinal ingredients often do not be transdermally absorbed sufficiently when conventional patches are used. Further, since the stratum corneum has a high lipid solubility, generally skin permeability of a medicine is extremely low.

Therefore, in order to enhance a transdermal absorption property of a medicine in the transdermal administration method, studies have been proceeded about composition and the like of an adhesive agent for use in a patch. As a part of them, such a patch is proposed that uses polymer material such as acrylic polymer or rubber polymer as an adhesive agent (JP-A-4-266821, JP-A-9-301854 and the like). Disclosure of the Invention However, when the aforementioned conventional patches are used, it can not necessarily be said that skin permeability of a medicine is sufficient. In addition, in these conventional patches, due to a fact that physical property of the formula such as cohesive and adhesive property of the adhesive layer is degraded when a transdermal absorption property of a medicine is enhanced, it is very difficult to satisfy all the characteristic features required as a patch. Further, property of medicines for use in a patch varies depending on kinds thereof and, on the other hand, compatibility of an adhesive agent to a specified medicine is not examined sufficiently yet.

The present invention was achieved in consideration of the problems included in the aforementioned conventional technique, and the object of the invention is to provide a patch employing oxybutynin and/or a pharmaceutically acceptable salt thereof as a medicine, wherein the patch can achieve both of a skin absorption property of the medicine and physical property of the formula at a high level.

The present inventors made efforts to achieve the aforementioned object, and found that many of acrylic polymer among polymer materials used in the conventional patch have a carboxyl group (—COOH) or a hydroxyl group (—OH) in the molecule as a reaction point for crosslinking, and that it is very difficult to make both of a skin absorption property of a medicine and physical property of the formula compatible. And, as the result of further efforts based on the knowledge, we found that the aforementioned problems can be dissolved by incorporating an acrylic polymer substantially free of both carboxyl group and hydroxyl group and rubber polymer in an adhesive layer at a specified ratio respectively in a patch employing oxybutynin and/or a pharmaceutically acceptable salt thereof as a medicine, to accomplish the invention.

Thus, the patch of the invention is a patch comprising a backing layer and an adhesive layer disposed on the backing layer and compounded with an adhesive agent and oxybutynin and/or a pharmaceutically acceptable salt thereof, wherein the adhesive agent comprises an acrylic polymer substantially free of both carboxyl group and hydroxyl group and rubber polymer at a weight ratio of content of the acrylic polymer to content of the rubber polymer of from 1:4 to 1:19.

In the invention, preferably the adhesive layer comprises 0.5-10% by weight of the acrylic polymer, 5-40% by weight of the rubber polymer and 10-60% by weight of an alicyclic saturated hydrocarbon resin-based tackifier on the basis of the total amount of compounds contained in the adhesive layer.

Further, in the invention, preferably a weight ratio of the total content of the acrylic polymer and the rubber polymer to content of the tackifier is from 1:1 to 1:3.

Further, in the invention, it is preferable that the acrylic polymer is at least one kind selected from: copolymer of polyacrylate including at least one selected from 2-ethylhexyl acrylate, butyl acrylate, diacetone acrylamide and tetraethylene glycol dimethacrylate, and polymethyl methacrylate; 2-ethylhexyl acrylate-N-vinyl-2-pyrrolidone-1,6-hexane glycol dimethacrylate terpolymer; aminoalkyl methacrylate copolymer E; and 2-ethylhexyl acrylate-vinyl acetate copolymer.

Further, in the invention, it is preferable that the rubber polymer is at least one kind selected from styrene-isoprene-styrene block copolymer, styrene-butadiene-styrene block copolymer, styrene-butadiene rubber, polyisobutylene, isoprene rubber and silicone rubber.

Furthermore, in the invention, preferably the rubber polymer is at least one kind selected from styrene-isoprene-styrene block copolymer and polyisobutylene.

Furthermore, in the invention, it is preferable that the acrylic polymer is at least one kind selected from 2-ethylhexyl acrylate-N-vinyl-2-pyrrolidone-1,6-hexane glycol dimethacrylate terpolymer and 2-ethylhexyl acrylate-vinyl acetate copolymer; and that the rubber polymer is styrene-isoprene-styrene block copolymer.

Still furthermore, in the invention, preferably a oxybutynin hydrochloride is compounded in the adhesive layer.

Still furthermore, in the invention, preferably the adhesive agent further comprises an organic acid, more preferably the organic acid is at least one kind selected from acetic acid and citric acid, and salts of these acids.

BEST MODE FOR CARRYING OUT THE INVENTION

Hereinafter, detailed explanation will be given about preferable embodiments of the invention.

The patch of the invention is a patch comprising a backing layer and an adhesive layer disposed on the backing layer and compounded with an adhesive agent and oxybutynin and/or a pharmaceutically acceptable salt thereof, wherein the adhesive agent comprises an acrylic polymer substantially free of both carboxyl group and hydroxyl group and rubber polymer at a weight ratio of content of the acrylic polymer to content of the rubber polymer of from 1:4 to 1:19.

As the backing layer for use in the patch of the invention, any one may be used without particular limitation insofar as it can support the adhesive layer, and an elastic and rigid backing layer may be used. Among them, one selected from woven cloth, nonwoven cloth and knitted cloth that have moisture permeability is preferable. Use of a backing layer having moisture permeability allows sweat accumulated between an affected part and the patch to effuse effectively and makes it possible to prevent stuffiness and skin irritation provided by the sweat. As such backing layer, specific examples include cloth and nonwoven cloth, polyurethane, polyester, polypropylene, polyvinyl acetate, polyvinylidene chloride, polyethylene, polyethylene terephthalate and aluminum sheet, one made up to woven cloth, nonwoven cloth or knitted cloth from synthetic or natural fiber such as nylon, acrylic, cotton, rayon or acetate or a complex thereof, and further conjugated material of these and film having moisture permeability and the like. Among them, knitted cloth made of polyester is preferably used from the point of safety, versatility and elasticity.

Thickness of the backing layer according to the invention is not particularly limited, but a thickness in a range of from 5 to 1000 μm is preferable. A thickness of the backing layer lower than the lowest limit described above tends to decrease operation easiness upon sticking the patch and, on the other hand, that higher than the highest limit described above tends to decrease production easiness in the production process of the patch due to difficulty of cutting the backing layer or the patch, or the like.

In a patch of the invention, an adhesive layer compounded with an adhesive agent and oxybutynin or a pharmaceutically acceptable salt thereof is disposed on the backing layer. Here, the adhesive agent according to the invention is an adhesive agent that comprises an acrylic polymer substantially free of both carboxyl group and hydroxyl group (hereinafter, simply referred to as "acrylic polymer" depending on the situation) and rubber polymer in the molecule.

In this connection, the acrylic polymer substantially free of both carboxyl group (carboxylic acid group, —COOH) and hydroxyl group (—OH) in the molecule according to the invention means an acrylic polymer that has no carboxyl group or hydroxyl group in the molecule thereof that could become a reaction point upon crosslinking. These polymers may be obtained by polymerizing monomers that have no carboxyl group and hydroxyl group. Examples of such monomer include methyl acrylate, ethyl acrylate, propyl acrylate, amyl acrylate, butyl acrylate, 2-ethylbutyl acrylate, hexyl acrylate, heptyl acrylate, octyl acrylate, nonyl acrylate, 2-ethylhexyl acrylate, decyl acrylate, dodecyl acrylate, tridecyl acrylate and, in addition, (meth)acrylic esters corresponding to targeted acrylic polymers, and the like.

Viscosity-average molecular weight of the acrylic polymer according to the invention is preferably 200000-1000000. A viscosity-average molecular weight of the acrylic polymer lower than the lowest limit described above tends to decrease physical property of the formula (especially cohesion property) and, on the other hand, that higher than the highest limit described above tends to decrease compatibility with other ingredients contained in the adhesive layer.

Preferable examples of the acrylic polymer according to the invention include:
(A1) block copolymer of polyacrylate including at least one kind selected from 2-ethylhexyl acrylate, butyl acrylate, diacetone acrylamide and tetraethylene glycol dimethacrylate, and polymethyl methacrylate,
(A2) 2-ethylhexyl acrylate-N-vinyl-2-pyrrolidone-1,6-hexane glycol dimethacrylate terpolymer,
(A3) aminoalkyl methacrylate copolymer E, and
(A4) 2-ethylhexyl acrylate-vinyl acetate copolymer.

Examples of commercial acrylic polymers substantially free of both carboxyl group and hydroxyl group include DURO-TAK87-2097 (having no functional group), DURO-TAK87-2194 (having no functional group) and DURO-TAK87-4098 (having no functional group) supplied by National Starch & Chemical, and the like. Among them, use of 2-ethylhexyl acrylate-N-vinyl-2-pyrrolidone-1,6-hexane glycol dimethacrylate terpolymer and/or 2-ethylhexyl acrylate-vinyl acetate copolymer is preferable because it tends to more enhance both of skin permeability of the medicine and physical property of the formula. These acrylic polymers may be used independently by one kind or in combination of two or more kinds.

In this connection, if a monomer having a carboxyl group or a hydroxyl group should exist in the raw monomer by a small amount as impurities, or when a side reaction such as thermal degradation should occur upon polymerization in a production process of the acrylic polymer described above, a carboxyl group or a hydroxyl group derived from the impurities will be introduced in the acrylic polymer to be obtained. However, such acrylic polymer is intended to be encompassed in the acrylic polymer substantially free of both carboxyl group and hydroxyl group, insofar as it does not damages a sufficiently high skin permeability of a medicine and a sufficiently high physical property of the formula, which belong to the patch of the invention.

However, it is preferable to decrease a carboxyl group and a hydroxyl group in the acrylic polymer according to the invention as far as possible, even if they are ones derived from contamination of impurities or from side reaction such as thermal degradation in the production process.

The rubber polymer according to the invention means natural or synthetic elastic polymer.

Preferable examples of such rubber polymer include:
(S1) styrene-isoprene-styrene block copolymer,
(S2) styrene-butadiene-styrene block copolymer,
(S3) styrene-butadiene rubber,
(S4) polyisobutylene,
(S5) isoprene rubber, and
(S6) silicone rubber.

Among them, use of styrene-isoprene-styrene block copolymer or polyisobutylene is more preferable because it tends to enhance both of skin permeability of the medicine and physical property of the formula. These rubber polymers may be used individually by one kind or in combination of two or more kinds.

Viscosity-average molecular weight of the rubber polymer according to the invention is preferably 30000-2500000, and more preferably 100000-1700000. A viscosity-average molecular weight lower than the lowest limit described above tends to decrease physical property of the formula (especially cohesion property) and, on the other hand, that higher than the highest limit described above tends to make production of a patch difficult because of decrease in compatibility with other ingredients contained in the adhesive layer.

Further, use of at least one kind selected from 2-ethylhexyl acrylate-N-vinyl-2-pyrrolidone-1,6-hexane glycol dimethacrylate terpolymer and 2-ethylhexyl acrylate-vinyl acetate copolymer as the acrylic polymer, and use of styrene-isoprene-styrene block copolymer as the rubber polymer respectively are preferred because both of skin permeability of the medicine and physical property of the formula are more enhanced.

In the invention, it is necessary that a weight ratio of content of the acrylic polymer substantially free of both carboxyl group and hydroxyl group in the molecule to content of the rubber polymer is in a range from 1:4 to 1:19. By determining the weight ratio of both contents in the aforementioned range, when oxybutynin and/or a pharmaceutically acceptable salt thereof as a medicine is compounded in the adhesive layer, skin permeability of the medicine is significantly enhanced and high-level physical properties of the formula become achievable. Furthermore, by determining the weight ratio of both contents in the aforementioned range, a moderate adhesive force is given to the adhesive layer, and adhesion to the skin and skin irritation are improved. In this connection, content of the rubber polymer less than 4 times that of the acrylic polymer gives insufficient skin permeability of the medicine. On the other hand, content of the rubber polymer more than 19 times that of the acrylic polymer gives insufficient physical property of the formula.

Content of the acrylic polymer according to the invention is not particularly limited insofar as the weight ratio of content of it to that of the rubber polymer is in the aforementioned range, but it is preferably 0.5-10% by weight, more preferably 1-5% by weight on the basis of the total amount of the adhesive agent. An amount of the acrylic polymer lower than the lowest limit described above tends to decrease skin permeability of the medicine and, on the other hand, that higher than the highest limit described above tends to decrease cohesion force of the adhesive layer.

Further, amount of the rubber polymer according to the invention is not particularly limited insofar as the weight ratio of content of it to that of the acrylic polymer is in the aforementioned range, but it is preferably 5-40% by weight, more preferably 10-25% by weight on the basis of the total amount of the adhesive agent. An amount of the rubber polymer lower than the lowest limit described above tends to decrease skin permeability of the medicine and, on the other hand, that higher than the highest limit described above tends to decrease adhesive force of the adhesive layer.

In this connection, in the invention, a rubber polymer such as ethylene-vinyl acetate copolymer (EVA, content of vinyl acetate: 5-60% by weight) may be further incorporated in the adhesive layer insofar as skin permeability of the medicine and physical property of the formula are not damaged. Content of such rubber polymer is preferably 0.05-1% by weight on the basis of the total amount of the compounds contained in the adhesive layer.

In the patch of the invention, oxybutynin and/or a pharmaceutically acceptable salt thereof is compounded in the adhesive layer as an active ingredient. When a pharmaceutically acceptable salt of oxybutynin is compounded, the salt may be either an inorganic salt or an organic salt. But hydrochloride salt (that is, oxybutynin hydrochloride) is especially preferable.

In the invention, amount of oxybutynin and/or a pharmaceutically acceptable salt thereof is preferably 0.1-50% by weight, more preferably 1-20% by weight on the basis of the total amount of the compounds contained in the adhesive layer. An amount of oxybutynin and/or a pharmaceutically acceptable salt thereof lower than the lowest limit described above tends to decrease skin permeability of the medicine and, on the other hand, that higher than the highest limit described above tends to decrease physical properties, because oxybutynin and/or a pharmaceutically acceptable salt thereof may not completely dissolve in the adhesive layer and crystallize.

The adhesive layer according to the invention is an adhesive layer comprising the aforementioned adhesive agent and the medicine and, in addition to these integrants, it may further comprise a tackifier. Specific examples of the tackifer for use in the invention include rosin derivatives (rosin, rosin glycerine ester, hydrogenated rosin, hydrogenated rosin glycerine ester, rosin pentaerythritol ester and the like), alicyclic saturated hydrocarbon resin (Arkon P100 (manufactured by Arakawa Chemical Industries) and the like), aliphatic hydrocarbon resin (Quintone B-170 (manufactured by ZEON CORPORATION) and the like), terpene resin (Clearon P-125 (manufactured by Yasuhara Chemical) and the like), maleic acid resin and the like. Among them, hydrogenated rosin glycerine ester, aliphatic hydrocarbon resin and terpene resin are preferable, and alicyclic saturated hydrocarbon resin is especially preferable.

Amount of the tackifier according to the invention is not particularly limited, but it is preferably 10-60% by weight, more preferably 30-50% by weight on the basis of the total amount of the compounds contained in the adhesive layer. An amount of the tackifier lower than the lowest limit described above tends to give an insufficient effect on enhancing adhesive force of the patch provided by compounding the tackifier and, on the other hand, that higher than the highest limit described above tends to increase skin irritation upon peeling the patch.

Further, in the case where an alicyclic saturated hydrocarbon resin is used as a tackifier, it is preferable that weight ratio of the total content of the acrylic polymer and the rubber polymer to content of the tackifier is from 1:1 to 1:3. When respective contents of the acrylic polymer, the rubber polymer and the tackifier satisfy the condition described above, both of skin permeability of oxybutynin and/or a pharmaceutically acceptable salt thereof and physical property of the formula are further enhanced and, in addition, adhesive force is further enhanced, to give a patch in which adhesive property and skin irritation have been further improved.

In the invention, the adhesive layer further comprises, preferably, an organic acid. Examples of such organic acid include aliphatic (mono-, di-, tri-) carboxylic acids (acetic acid, propionic acid, citric acid (including anhydrous citric acid), isobutyric acid, caproic acid, caprylic acid, lactic acid, maleic acid, pyruvic acid, oxalic acid, succinic acid, tartaric acid and the like), aromatic carboxylic acids (phthalic acid, salicylic acid, benzoic acid, acetyl salicylic acid and the like), alkyl sulfonic acids (methane sulfonic acid, ethane sulfonic acid, propyl sulfonic acid, butane sulfonic acid, polyoxyethylenealkyl ether sulfonate and the like), alkyl sulfonic acid derivatives (N-2-hydroxyethylpiperidine-N'-2-ethane sulfonic acid, cholic acid derivatives (dehydrocholic acid and the like), and salts thereof (for example, alkali metal salts such as sodium salts), and the like. Among these organic acids, carboxylic acids and salts thereof are preferable, and acetic acid, sodium acetate and citric acid are especially preferable. These organic acids may be used individually by one kind or in mixture of two or more kinds.

In the adhesive layer according to the invention, content of the organic acids is not particularly limited, but it is preferably 0.01-20% by weight, more preferably 0.1-15% by weight, and furthermore preferably 0.1-12% by weight on the basis of the total amount of the compounds contained in the adhesive layer. A content of the organic acid lower than the lowest limit described above tends to give an insufficient effect on enhancing skin permeability of the medicine provided by the organic acid and, on the other hand, that higher than the highest limit described above tends to increase skin irritating property.

The adhesive layer according to the invention may further comprise a skin permeation enhancer. As such permeation enhancer, compounds conventionally recognized to have an absorption enhancing effect on the skin may be used, including specifically the following having 6 to 20 carbon atoms as fatty acids, aliphatic alcohols, fatty acid esters, fatty acid amides, and fatty acid ethers, aromatic organic acids, aromatic alcohols, aromatic organic acid esters and ethers, which may be saturated or unsaturated, and also may be linear, branched or cyclic. Further, in the invention, lactic acid esters, acetic acid esters, monoterpenes, sesquiterpenes, Azone, Azone derivatives, glycerin fatty acid esters, propylene glycol fatty acid esters, sorbitan fatty acid esters (Span), polysorbates (Tween), polyethylene glycol fatty acid esters, polyoxyethylene hydrogenated castor oils (HCO), polyoxyethylene alkyl ethers, sucrose fatty acid esters or vegetable oils may be used as an absorption enhancer.

Among these absorption enhancers, preferable examples include caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methyl laurate, hexyl laurate, lauric acid diethanol amide, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, L-menthol, borneol, d-limonene, isoeugenol, isoborneol, nerol, dl-camphor, glycerin monocaprirate, glycerin monocaprate, glycerin monolaurate, glycerin monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-60, pirotiodecane and olive oil. And, lauryl alcohol, myristyl alcohol, isostearyl alcohol, lauric acid diethanol amide, glycerin monocaprirate, glycerin monocaprate, glycerin monooleate, sorbitan monolaurate, propylene glycol monolaurate, polyoxyethylene lauryl ether and pirotiodecane are more preferable. Such absorption enhancers may be used independently by one kind, or may be used in combination of two or more kinds.

In the adhesive layer according to the invention, content of the absorption enhancer is not particularly limited, but it is preferably 0.01-20% by weight, more preferably 0.05-10% by weight, and furthermore preferably 0.1-5% by weight on the basis of the total weight of the compounds contained in the adhesive layer. A content of the absorption enhancer lower than the lowest limit described above tends to give an insufficient effect on enhancing skin permeability of the medicine provided by the absorption enhancer and, on the other hand, that higher than the highest limit described above tends to increase irritating property to skin on edema and the like.

The adhesive layer according to the invention may further comprise a plasticizer. Specific examples of such plasticizer include petroleum oils (paraffin process oils, naphthene process oils, aromatic process oils and the like), squalane, squalene, vegetable oils (olive oil, camellia oil, castor oil, tall oil, peanut oil), silicone oil, liquid rubber (polybutane, liquid isoprene rubber), liquid fatty acid esters (isopropyl myristate, hexyl laurate, diethyl sebacate, diisopropyl sebacate and the like), diethylene glycol, polyethylene glycol, propylene glycol, dipropylene glycol, triacetin, triethyl citrate, crotamiton and the like. Among these plasticizers, liquid paraffin, liquid polybutene, crotamiton, diethyl sebacate and hexyl laurate are especially preferable. These plasticizers may be used individually by one kind or in combination of two or more kinds.

In the adhesive layer according to the invention, content of the plasticizer is not particularly limited, but it is preferably 5-70% by weight, more preferably 10-60% by weight, and furthermore preferably 10-50% by weight on the basis of the total amount of the compounds contained in the adhesive layer. A content of the plasticizer lower than the lower limit described above tends to give an insufficient effect on enhancing cohesion force of the patch provided by compounding a plasticizer and, on the other hand, that higher than the highest limit described above tends to give an insufficient skin permeability of the medicine.

Further, in the invention, the adhesive layer may incorporates an antioxidant, a filler, a ultraviolet absorbent or the like if necessary.

Preferable examples of the antioxidant according to the invention include tocopherols and ester derivatives thereof, ascorbic acid, ascorbic acid-stearic acid ester, nordihydroguaiaretic acid, dibutylhydroxytoluene (BHT) and butylhydroxyanisol.

Preferable examples of the filler include calcium carbonate, magnesium carbonate, silicates (such as aluminum silicate and magnesium silicate), silicic acid, barium sulfate, calcium sulfate, calcium zincate, zinc oxide and titanium oxide.

Preferable examples of the ultraviolet absorbent include p-aminobenzoic acid derivatives, anthranilic acid derivatives, salicylic acid derivatives, coumarin derivatives, amino acid-series compounds, imidazoline derivatives, pyrimidine derivatives and dioxane derivatives.

In the adhesive layer according to the invention, respective contents of the antioxidant, the filler and the ultraviolet absorbent are not particularly limited, but the total amount of contents of the antioxidant, the filler and the ultraviolet absorbent is preferably 0-10% by weight, more preferably 0-5% by weight, and furthermore preferably 0-2% by weight on the basis of the total amount of the compounds contained in the adhesive layer.

When forming the adhesive layer having the aforementioned constitution on the backing layer, the forming method is not particularly limited and, for example, the patch of the invention can be obtained by thermally melting a mixture of the adhesive agent, oxybutynin and/or a pharmaceutically acceptable salt thereof and other ingredients described above that are added according to need, and by coating the molten mixture on the backing layer. Further, when the patch of the invention further comprises release liner on the adhesive layer, the thermally molten mixture described above is coated on the release liner followed by laminating the backing layer on the coated side, or the thermally molten mixture described above is coated on the backing layer followed by laying the release liner on the coated side, to give the patch of the invention. Furthermore, instead of thermally melting the mixture described above, it is also possible to use a coating liquid prepared by dissolving the above mentioned mixture in a solvent such as toluene, hexane or ethyl acetate to give the patch of the invention.

The patch of the invention may be a patch provided with one adhesive layer, or one provided with two or more adhesive layers insofar as they do not degrade skin permeability of oxybutynin and/or a pharmaceutically acceptable salt thereof.

Further, thickness of the adhesive layer according to the invention is not particularly limited, but it is preferably 20-200 μm. A thickness of the adhesive layer lower than the lowest limit described above tends to give an insufficient skin permeability of the medicine and, on the other hand, that higher than the highest limit described above tends to generate a phenomenon in which the adhesive agent remains adhering to the skin after application (adhesive agent remaining).

Furthermore, when the patch of the invention comprises release liner, specific examples of such release liner include film made of polyester such as polyethylene terephthalate, polyvinyl chloride, polyvinylidene chloride or the like, and laminate film of fine paper and polyolefin. In these release liners, it is preferable to provide silicone treatment to the side contacting the adhesive layer, because operation easiness upon peeling the release liner off the adhesive agent is enhanced.

The invention will be explained further specifically on the basis of Examples and Comparative Examples, however the invention is not limited to these examples.

Example 1

Oxybutynin hydrochloride, sodium acetate, anhydrous citric acid and liquid paraffin were charged in a mortar and mixed sufficiently. The mixture was added to a mixed liquid consisting of an acrylic polymer substantially free of both carboxyl group and hydroxyl group (2-ethylhexyl acrylate-vinyl acetate copolymer), styrene-isoprene-styrene block copolymer, alicyclic saturated hydrocarbon resin, ethyl acetate and toluene to prepare a coating liquid for an adhesive layer. Contents of respective ingredients (values on the basis of the total amount of the compounds excluding toluene) and weight ration of content of the acrylic polymer to that of the rubber polymer in the obtained coating liquid are listed in Table 1.

the receptor side, where a water of 37° C. was circulating the periphery of the cell. Next, a patch (formulation applying area of 5 cm$^2$) was stuck to the stratum corneum side of the skin. While using normal saline as a receptor layer, sampling of the receptor solution was carried out at a speed of 5 mL/hour every 2 hours up to 24 hours. For receptor solutions obtained at respective times, the flow volume was measured, and medicine concentration was measured by using high-performance liquid chromatography. From the obtained measurement values, permeation rate per 1 hour was calculated to obtain medicine permeation rate per unit area of the skin at steady state. The respective maximum values of the medicine permeation rate (maximum skin permeation rate) obtained in the period from the start of the test to 24 hours are listed in Table 1.

(Test for Physical Property of the Formula)

For respective patches obtained in Examples 1-2 and Comparative Examples 1-3, measurement of adhesive force with a probe tack tester and peel testing machine, and measurement of cohesion force (holding power) with a creep measuring machine were carried out to evaluate physical property of the formula on the basis of the following standard:

A: both adhesion force and cohesion force are sufficient

B: at least one of adhesion force and cohesion force is insufficient.

The obtained results are listed in Table 1.

TABLE 1

| | | Example 1 | Example 2 | Comparative Example 1 | Comparative Example 2 | Comparative Example 3 |
|---|---|---|---|---|---|---|
| Composition [% by weight] | Styrene-isoprene-styrene copolymer | 22.5 | 20.0 | 25.0 | 20.9 | 12.5 |
| | 2-Ethylhexyl acrylate-vinyl acetate copolymer | 2.5 | 5.0 | — | 9.1 | 12.5 |
| | Alicyclic hydrocarbon resin | 40.0 | 40.0 | 40.0 | 40.0 | 40.0 |
| | Liquid paraffin | 16.0 | 16.0 | 16.0 | 16.0 | 16.0 |
| | Oxybutynin hydrochloride | 15.0 | 15.0 | 15.0 | 15.0 | 15.0 |
| | Sodium acetate | 3.0 | 3.0 | 3.0 | 3.0 | 3.0 |
| | Anhydrous citric acid | 1.0 | 1.0 | 1.0 | 1.0 | 1.0 |
| Weight ratio of acrylic polymer to rubber polymer | | 1:9 | 1:4 | 0:10 | 1:2.3 | 1:1 |
| Maximum skin permeation rate [μg/cm$^2$/hr] | | 16.2 | 15.8 | 6.9 | 11 | 8.8 |
| Physical property of the formula | | A | A | B | B | B |

Next, the obtained adhesive mass solution was coated onto a release liner made of polyethylene terephthalate and dried to remove the solvent to form an adhesive layer. Then, knitted cloth made of polyester as the backing layer was laminated to the adhesive layer to give a targeted patch.

Example 2

Comparative Example 1-3

In Example 2 and Comparative Example 1-3, patches were prepared in the same way as Example 1 except that respective contents of 2-ethylhexyl acrylate-vinyl acetate copolymer and styrene-isoprene-styrene block copolymer were determined as listed in Table 1.

(Skin Permeability Test)

Using respective patches obtained in Examples 1-2 and Comparative Examples 1-3, following tests were carried out.

First, dorsal skin of a hairless mouse was extirpated, which was set to a flow-through-cell with facing the dermis side to As listed in Table 1, it was confirmed that skin permeability of oxybutynin hydrochloride and physical property of the formula are made compatible at a high level in respective patches in Examples 1-2. On the contrary, both of skin permeability and physical property of the formula were insufficient in the case of respective patches in Comparative Examples 1-3. Further, respective patches in Comparative Examples 2-3 had a low cohesion force and generated cohesion failure.

Examples 3-5

In Examples 3-5, patches were prepared in the same way as Example 1 except that respective compositions of coating liquids for the adhesive layer were determined as listed in Table 2.

Comparative Example 4

In Comparative Example 4, a patch was prepared in the same way as Example 1 except that an acrylic polymer with a hydroxyl group (Duro-TAK87-2287) was used in place of 2-ethylhexyl acrylate-vinyl acetate copolymer, and that composition of coating liquid for the adhesive layer was determined as listed in Table 2.

Comparative Example 5

In Comparative Example 5, a patch was prepared in the same way as Example 1 except that an acrylic polymer with a carboxyl group (Duro-TAK87-2852) was used in place of 2-ethylhexyl acrylate-vinyl acetate copolymer, and that composition of coating liquid for the adhesive layer was determined as listed in Table 2.

Next, by using respective patches obtained in Examples 3-5 and Comparative Examples 4-5, skin permeability test and physical property of the formula test were carried out in the same way as Example 1. The obtained results are listed in Table 2.

TABLE 2

|  |  | Example 3 | Example 4 | Example 5 | Comparative Example 4 | Comparative Example 5 |
|---|---|---|---|---|---|---|
| Composition [% by weight] | Styrene-isoprene-styrene copolymer | 20.7 | 20.7 | 23.75 | 20.7 | 20.7 |
|  | 2-Ethylhexyl acrylate-vinyl acetate copolymer | 2.3 | 2.3 | 1.25 | — | — |
|  | Duro-TAK87-2287 | — | — | — | 2.3 | — |
|  | Duro-TAK87-2852 | — | — | — | — | 2.3 |
|  | Alicyclic hydrocarbon resin | 40.7 | 37.0 | 40.0 | 37.0 | 37.0 |
|  | Liquid paraffin | 13.5 | 13.5 | 16.0 | 13.5 | 13.5 |
|  | Oxybutynin hydrochloride | 15.0 | 15.0 | 15.0 | 15.0 | 15.0 |
|  | Sodium acetate | 6.0 | 9.0 | 3.0 | 9.0 | 9.0 |
|  | Anhydrous citric acid | 1.8 | 2.5 | 1.0 | 2.5 | 2.5 |
| Weight ratio of acrylic polymer to rubber polymer |  | 1:9 | 1:9 | 1:19 | 1:9 | 1:9 |
| Maximum skin permeation rate [μg/cm$^2$/hr] |  | 23.6 | 28.8 | 14.9 | 11.7 | 9.7 |
| Physical property of the formula |  | A | A | A | A | A |

As listed in Table 2, in respective patches in Examples 3-5, by determining respective contents of sodium acetate as 6% and 9%, further enhancement of skin permeability of the medicine could be achieved. On the contrary, in the case of Comparative Examples 4-5 in which an acrylic polymer with a hydroxyl group or a carboxyl group was used, skin permeability of the medicine was insufficient even when content of sodium acetate was 9%.

INDUSTRIAL APPLICABILITY

As explained above, according to the invention, upon using oxybutynin and or a pharmaceutically acceptable salt thereof as a medicine, a patch that can achieve both of skin permeability of the medicine and physical property of the formula at a high level is provided.

The invention claimed is:
1. A patch comprising a backing layer and an adhesive layer disposed on the backing layer,
the adhesive layer consisting of
an adhesive agent;
oxybutynin and/or a pharmaceutically acceptable salt thereof;
one or more pharmaceutically acceptable excipient selected from the group consisting of an organic acid, a skin permeation enhancer, an absorption enhancer, a plasticizer, a tackifier, an antioxidant, a filler and an ultraviolet absorber;
1-5% by weight of a 2-ethylhexyl acrylate-vinyl acetate copolymer based on the total weight of the adhesive agent, the 2-ethylhexyl acrylate-vinyl acetate copolymer being substantially free of both carboxyl groups and hydroxyl groups in the molecule; and
10-25% by weight of a styrene-isoprene-styrene block copolymer based on the total weight of the adhesive agent,
wherein the weight ratio of the 2-ethylhexyl acrylate-vinyl acetate copolymer to the styrene-isoprene-styrene block copolymer is from 1:4 to 1:19.
2. A patch comprising a backing layer and an adhesive layer disposed on the backing layer,
the adhesive layer consisting of:
an adhesive agent;
oxybutynin and/or a pharmaceutically acceptable salt thereof;
one or more pharmaceutically acceptable excipient selected from the group consisting of an organic acid, a skin permeation enhancer, an absorption enhancer, a plasticizer, a tackifier, an antioxidant, a filler, and a ultraviolet absorber;
1-5% by weight of a 2-ethylhexyl acrylate-vinyl acetate copolymer based on the total weight of the adhesive agent, the 2-ethylhexyl acrylate-vinyl acetate copolymer being substantially free of both carboxyl groups and hydroxyl groups in the molecule; and
10-25% by weight of a styrene-isoprene-styrene block copolymer based on the total weight of the adhesive agent;
wherein the weight ratio of the 2-ethylhexyl acrylate-vinyl acetate copolymer to the styrene-isoprene-styrene block copolymer is from 1:4 to 1:19; and
10-60% by weight of an alicyclic saturated hydrocarbon resin-based tackifier, based on the total weight of the compounds contained in the adhesive layer.

3. The patch according to claim 2, wherein weight ratio of the 2-ethylhexyl acrylate-vinyl acetate copolymer to the tackifier is from 1:1 to 1:3.

4. The patch according to claim 1, wherein the adhesive layer is compounded with oxybutynin hydrochloride.

5. The patch according to claim 1, wherein the organic acid is at least one selected from the group consisting of acetic acid, citric acid and salts thereof.

* * * * *